(12) United States Patent
Lemperle et al.

(10) Patent No.: US 6,391,059 B1
(45) Date of Patent: May 21, 2002

(54) MEMBRANE WITH TISSUE-GUIDING SURFACE CORRUGATIONS

(75) Inventors: Stefan M. Lemperle, La Jolla; Christopher J. Calhoun, San Diego, both of CA (US)

(73) Assignee: MacroPore, Inc., San Diego, CA (US)

( * ) Notice: Subject to any disclaimer, the term of this patent is extended or adjusted under 35 U.S.C. 154(b) by 0 days.

(21) Appl. No.: 09/673,164
(22) PCT Filed: Apr. 7, 1999
(86) PCT No.: PCT/US99/07655
 § 371 Date: Oct. 6, 2000
 § 102(e) Date: Oct. 6, 2000
(87) PCT Pub. No.: WO99/51171
 PCT Pub. Date: Oct. 14, 1999

Related U.S. Application Data

(60) Provisional application No. 60/081,006, filed on Apr. 7, 1998.

(51) Int. Cl.⁷ .................................................. A61F 2/36
(52) U.S. Cl. ..................... 623/23.5; 623/11.11; 606/151
(58) Field of Search .......................... 623/11.11, 16.11, 623/23.74, 23.5; 606/60, 69, 70, 74, 86, 151, 154

(56) References Cited

U.S. PATENT DOCUMENTS 5,380,328 A * 1/1995 Morgan
5,443,483 A * 8/1995 Kirsch
5,676,699 A * 10/1997 Gogolewski et al.
5,919,232 A * 7/1999 Chaffringeon et al.
5,980,540 A * 11/1999 Bruce
6,071,291 A * 6/2000 Forst et al.
6,113,623 A * 9/2000 Sgro

* cited by examiner

Primary Examiner—Pedro Philogene
(74) Attorney, Agent, or Firm—Stout, Uxa, Buyan & Mullins, LLP

(57) ABSTRACT

A resorbing, flexible implant in the form of a continuous macro-porous sheet (42) is disclosed. The implant is adapted to protect biological tissue defects, especially bone defects in the mammalian skeletal system, from the interposition of adjacent soft tissues during in vitro repair. The membrane (42) has pores with diameters from 20 microns to 3000 microns. This porosity is such that vasculature, and connective tissue cells derived from the adjacent soft tissues including the periosteum, can proliferate through the membrane into the bone defect. The thickness of the sheet is such that the sheet has both sufficient flexibility to allow the sheet to be shaped to conform to the configuration of a skeletal region to be repaired, and sufficient tensile strength to allow the sheet to be so shaped without damage to the sheet. The sheet provides enough inherent mechanical strength to withstand pressure from adjacent musculature, and does not collapse.

39 Claims, 12 Drawing Sheets

MEMBRANE WITH TISSUE-GUIDING SURFACE CORRUGATIONS

This Appln is a 371 of PCT/US99/07655 filed Apr. 7, 1999 which claims benefit of Prov. No. 60/081,006 filed Apr. 7, 1998.

BACKGROUND OF THE INVENTION

1. Field of the Invention

The present invention relates generally to implants for use in repairing various portions of the mammalian skeletal system and, more particularly, to implants for use in clinical procedures such as bone fracture repair, regeneration of bone loss, augmentation of deficient bone, and related procedures.

2. Description of Related Art

Various types of defects in the mammalian skeletal system can be treated by various surgical procedures. Defects in the mammalian skeletal system may include bone fracture, loss of bone occurring from traumatic, surgical, or infectious sources, and bone deficiencies stemming from conditions such as atrophy and congenital anomalies.

One procedure that is common in the prior art for treating bone defects involves the placement of additional bone into the bone defect area. This procedure, which is commonly referred to as bone grafting, is the second most frequently performed surgical grafting procedure, with skin grafting the most common surgical grafting procedure. Current bone grafting procedures include the use of vascularized or non-vascularized autografts and allografts.

A bone autograft is a portion of bone taken from another area of the skeletal system of the patient. A bone allograft, in contrast, involves a human donor source other than the recipient patient. Allogenic bone graft typically comprises bone harvested from cadavers, which is subsequently treated and stored in a bone bank and ultimately used as a bone graft implant. Allogenic bone graft is known to have osteoconductive and osteoinductive capabilities, although the osteoinductive properties are limited because of the necessary tissue sterilizing and cleaning procedures associated with harvesting these bone grafts. The term osteoconduction refers to a class of biomaterials which provide a three-dimensional porous framework to conduct the ingrowth of new living bone into this structure. The term osteoinduction refers to a class of materials having capabilities of recruiting mesenchymal stem cells of the patient and promoting their differentiation into osteoblasts, which are bone forming cells. An osteoinductive material will typically form bone if implanted into an area where bone would not normally grow. For example, the placement of bone morphogenic proteins into the muscle of a patient will result in ectopic (outside of bone) bone formation.

Both bone autografting procedures and bone allografting procedures are associated with shortcomings in the healing of bone defects within the mammalian skeletal system. Bone autografting procedures are typically associated with limitation of donor sites, bone quantity, and donor site morbidity (especially if multiple donor sites are required). Bone allografting procedures, to begin with, only have limited osteoinductive capabilities. In addition to the very limited osteoinduction properties of allogenic bone grafts, compared to autograft samples, allografts are immunogenic to a certain degree, bear the risk of disease transmission (e.g. HIV and Hepatitis), and, depending on the size of the allograft, require a long time for ingrowth and partial substitution with new bone. This long substitution process often requires a time duration of greater than one year before satisfactory clinical results are obtained. Additionally, pressure from the adjacent musculature may dislocate bone graft material. Bone grafts may refracture after fixator removal if bone ingrowth and substitution is inadequate.

As a substitute to actual bone grafts, which include autografts and allografts, various bone graft substitutes have been used by the prior art for treating bone defects in the mammalian skeletal system.

Porous ceramic bone graft substitutes, for instance, such as coralline hydroxyapatites, operate similarly to bone grafts by providing a three-dimensional structural framework. This framework conducts the regenerating bone of the patient into the porous matrix of the three-dimensional structural framework. This process of conducting the regenerating bone into the porous matrix is commonly referred to as osteoconduction, as opposed to osteoinduction discussed above. Permanent, non-resorbable, inorganic, ceramic implants have shortcomings such as inherent brittleness and large framework volume fractions. The framework volume fraction of a typical bone graft substitute comprises approximately 40 percent of the volume where new bone could otherwise grow. This 40 percent volume occupied by a bone graft substitute, consequently, cannot be occupied by the regenerating bone of the patient.

A process referred to as guided tissue regeneration is widely used by periodontists to regenerate bone and periodontal ligaments (ligaments between the tooth root and the bone) around dental implants, for example. This surgical procedure uses cell-occlusive (cells cannot pass through) but fluid-permeable membranes, which are otherwise known as semipermeable membranes, in order to cover and segregate a bone defect from the surrounding soft tissues. U.S. Pat. No. 3,962,153 discloses such a cell-occlusive, fluid-permeable membrane. Use of these cell-occlusive, fluid permeable membranes, has been predominantly developed and used by periodontists over the last decade, who worked in the mouth around teeth. The human body has many tissue types which originate from three primary germ layers of the embryo: the ectoderm, the mesoderm and the entoderm. From the ectoderm are derived the skin and its attached tissues, such as nails, hair and glands of the skin, the nervous system, external sense organs and the epithelial lining of the mouth and anus. From the mesoderm are derived the connective tissues, bone, cartilage, muscle, blood and blood vessels. From the entoderm are derived, among others, the digestive tract, bladder and urethra. The "precursor" cells of these layers are limited to only becoming cells of their respective tissue type. Bone, muscle, connective tissue, blood vessels and cartilage are of mesenchymal origin which means from the meshwork of embryonic connective tissue in the mesoderm, and are formed from versatile mesenchymal stem cells, whereas the lining of the mouth is of ectodermal origin and is formed of epithelial cells derived from the ectoderm. Ectodermal cells do not have the potential to become bone forming cells and, conversely, mesenchymal cells do not have the potential to form epithelium.

Epithelial cells are present in the mouth, but are not present in many other areas of the mammalian skeletal system, such as areas near long bones of the mammalian skeleton. The development of cell-occlusive, fluid permeable membranes was developed in the context of periodontal and oral applications, for the purpose of excluding the introduction of epithelial cells into the bone defect area of the patient because they are believed to hinder bone formation. Epithelial cells proliferate faster than bone cells and, therefore, the exclusion of these epithelial cells from the bone defect area has been considered to be essential for optimal bone and ligament regeneration in these periodontal and oral applications. Although cell-occlusive, fluid permeable membranes have been predominantly used in periodontal and oral applications, these cell-occlusive membranes have recently also been applied for tissue segregation in other defect sites in the mammalian skeletal system, such as long bone defects.

These cell-occlusive membranes of the prior art have a shortcoming of blocking blood vessels and mesenchymal cells from entering into the bone defect area. Thus, the advantage of precluding epithelial cells from the bone defect area in the oral cavity is achieved at the expense of also precluding entry of blood vessels and surrounding mesenchymal cells into the bone defect area, as well. In periodontal and oral applications, the advantage of precluding epithelial cells is believed to be worth the shortcoming of also precluding blood vessels and surrounding mesenchymal cells from the bone defect area. In other areas of the mammalian skeletal system, however, where epithelial cells are not present, these cell-occlusive, fluid-permeable membranes preclude the introduction of blood vessels and surrounding mesenchymal cells for no apparent reason. Thus, a need has existed in the prior art for a cell-permeable membrane barrier to protect non-periodontal bone defects from gross soft tissue prolapse and to thereby facilitate bone regeneration.

Turning to FIG. 1, a typical cell-occlusive, fluid permeable membrane 10 is illustrated surrounding a first section of the long bone 12 and a second section of long bone 14. The bone defect area 20 is bounded by the two ends 16, 18 of the first section of long bone 12 and the second section of long bone 14, respectively, and by the cell-occlusive, fluid-permeable membrane 10. Although this bone defect area 20 can receive blood from the bone vessels 23, blood and cells from the surrounding blood vessels 25 and tissues 27 is precluded from entering the bone defect area 20. The periosteum 31 and the surrounding tissues 27 are just external to the cell-occlusive, fluid-permeable membrane 10 and are guided in the directions of the arrows A1 and A2.

In addition to being cell-occlusive, the cell-occlusive, fluid permeable membrane 10 suffers from a lack of rigidity, as evidenced by the hour-glass configuration of the cell-occlusive, fluid-permeable membrane 10 in FIG. 1. A typical thickness of the cell-occlusive, fluid-permeable membrane 10 comprises less than 5 microns. Since periodontal defects are typically small, and since oral soft tissues typically do not apply much pressure, the cell-occlusive, fluid-permeable membrane 10 of the prior art has maintained its very thin and flexible configuration. Unfortunately, this very thin and flexible configuration, which is somewhat suitable for periodontal and oral applications, is not suitable for maintaining and protecting a sufficiently large bone defect area 20 in non-periodontal and non-oral applications. Since muscles are much larger and more powerful in orthopedic applications, for example, the cell-occlusive, fluid-permeable membrane 10 cannot provide sufficient protection against the prolapse of soft tissues into the bone defect area 20. When the surrounding tissues prolapse into the bone defect area 20, these interposed tissues present a physical barrier for the regenerating bone. The regenerating bone will not be able to push the interposed soft tissues out of the bone defect area, and subsequently, further regeneration of the bone in these areas occupied by the prolapsed soft tissues is prevented. A "non-union" (or pseudoarthrosis which means pseudo-joint) may result, comprising fibrous scar tissue instead of bone. Additionally, the prior art cell-occlusive, fluid-permeable membrane 10 is non-resorbable, and cannot be absorbed by the patient's body. Consequently, in order to avoid the risk of bacterial infection, the cell-occlusive, fluid-permeable membrane 10 must be removed during a subsequent operation, which may introduce further complications and risks to the patient. Thus, in addition to being cell-occlusive, prior membranes suffer from lack of inherent strength and non-resorbability.

A few other devices have been developed in the prior art for treating bone defects, but these devices comprise either fixation devices or prosthetic devices. A fixation device, comprising a titanium screen mesh, is disclosed in U.S. Pat. No. 5,346,492. This titanium screen mesh forms a fixation device, which is designed to be non-resorbable. The fixation device comprises a metallic plate structure which provides the necessary strength, at the cost of being non-resorbable. To date, any known resorbable material would not be capable of providing the equivalent rigidity and function of the titanium mesh screen. The metallic plate structure of the fixation device comprises a number of perforations designed specifically for accommodating screws for fixation. These screw perforations have diameters (between 4.8 millimeters and 17.5 millimeters), which do not prevent gross prolapse of soft tissues into the bone defect area. Such gross prolapse of soft tissues occupies space which would otherwise be filled with new bone. The physical barrier presented by the prolapsing soft tissues greatly impairs new bone formation within the bone defect area. The fixation device is secured onto the bone of the patient with the screws and is designed to be permanently left inside the patient. Any proliferation of blood vessels through these screw holes would be destroyed by any subsequent removal of the fixation device. On the other hand, if the fixation device is left in permanently, which is a disclosed embodiment, the bone of the patient will be permanently stress shielded. In other words, the mended bone, after initial healing will subsequently start to resorb, since this new bone is not exposed to functional (mechanical) stress. The fixation device, if left in the patient, will shield the bone defect area from functional stress and thus prevent an optimal amount of new bone formation.

A prosthetic device, which comprises holes punched into a planar material for facilitating suturing of the prosthetic device, is disclosed in U.S. Pat. No. 5,222,987. This prosthetic device, however, is only disclosed in the context of fabricating artificial bone structure. In other words, this prosthetic device is not used in any process associated with bone regeneration. The prosthetic device comprises a fabric-like composite onto which a polymer or resin is added, before the resulting product is molded into the shape of a bone. A polymerizable initiator is subsequently added to harden and bond the materials together. Small holes or ports may be added to accommodate sutures for attaching the prosthetic device to the body. The prosthetic device is specifically designed as a replacement for the rib cage of a mammalian skeletal system, and does not facilitate bone regeneration.

Other porous devices, in addition to the above-mentioned fixation and prosthetic devices, have been implemented by the prior art. One such device, which is disclosed in U.S. Pat. Nos. 5,306,304, 5,464,439, and 4,932,973, disclose an allogenic bone graft membrane having pores therein. The allogenic bone graft membrane is disclosed in these patents as providing a filler for bone defects. The matrix-like properties of the allogenic bone graft provide osteoconduction, and the morphogenic proteins within the allogenic bone graft provide osteoinductive properties. As mentioned before, an allogenic bone graft is typically harvested from a human cadaver and subsequently processed for implantation. The allogenic bone graft is intended to become integrated with the new bone of a patient and partially remodeled over time into a composite of both cadaver bone and new regenerated natural bone, while permanently remaining within the bone defect area of the patient. The pores in the allogenic bone graft membrane of these patents are designed to maximize the exposed surface area in order to enhance its osteoinductive contribution, as bone morphogenic proteins are released from the surface of the allogenic bone graft. This allogenic bone graft matrix will never be completely resorbed. This is obviously disadvantageous, because its structure reduces the space for new bone regeneration.

Another device, which comprises apertures or pores for facilitating tissue growth therein, is disclosed in U.S. Pat. No. 5,326,356. This patent is directed to an apparatus for generating artificial skin grafts. Bio-compatible membranes comprising natural, synthetic, or semi-synthetic origin are used as a support for the in vitro (outside of a living organism) growth of epithelial skin cells. These epithelial skin cells are grown into the pores of the membrane outside of the body of the patient. The resulting artificial skin graft is obviously not intended for use on the mammalian skeletal system. This artificial skin graft, in any event, would be far too thin and flexible for use on the mammalian skeletal system, and further would not have adequate fixation strength. Moreover, the epithelial cells which comprise the artificial skin graft are not present in the non-periodontal and non-oral applications, such as long bones, where a cell-permeable membrane is needed in the prior art for facilitating bone regeneration.

SUMMARY OF THE INVENTION

The present invention recognizes that a cell-occlusive, fluid permeable membrane is not suitable for bone regeneration in non-periodontal and non-oral applications. In addition to lacking rigidity and resorbability, the present invention recognizes that these prior art cell-occlusive, fluid-permeable membranes hinder bone regeneration by blocking the ingress of blood vessels and cells into the bone defect area. The protective bone regeneration membrane of the present invention has a much smaller net surface area, compared to prior art cell-occlusive, fluid permeable membranes, resulting from the introduction of cell-permeable apertures into the membrane of the present invention. In addition to having a smaller net surface area, the protective bone regeneration membrane of the present invention is substantially stronger and more rigid than prior art cell-occlusive, fluid permeable membranes.

According to one aspect of the present invention, an implant for protecting biological tissue defects from a prolapse of adjacent soft tissues during in vivo repair of the biological tissue defects includes a substantially planar sheet of non-metallic base material. The implant further includes a plurality of apertures disposed in the substantially-planar sheet of non-metallic base material. The apertures are adapted for allowing a proliferation of vasculature and connective tissue cells, derived from the adjacent soft tissues, into the biological tissue defect, while preventing any gross prolapse of the adjacent soft tissues into the biological tissue defect. The connective tissue cells include mesenchymal cells, and the implant may be impregnated with at least one substance for cellular control. This substance for cellular control may include at least one of a chemotactic substance for influencing cell-migration, an inhibitory substance for influencing cell-migration, a mitogenic growth factor for influencing cell proliferation, a growth factor for influencing cell differentiation, and factors which promote neoangiogenesis (formation of new blood vessels). The biological tissue defect preferably comprises a bone defect and, more preferably, comprises a non-periodontal, non-oral bone defect.

The implant may be used in combination with a fixation device for stabilizing the bone defect. The material of the implant is flexible enough to conform to a curvature of a bone and strong enough to reduce macro-motion of the bone defect and limit transmission of surrounding motion into the interior space when the fixation device is attached to the bone defect. The implant is adapted for protecting the bone defect from a prolapse of adjacent soft tissues into the bone defect during repair of the bone defect and, further, is adapted for preventing stress shielded resorption of bone after the repair of the bone defect. The bone, which is prevented from being resorbed, may include either an autograft, an allograft, and/or new regenerated bone within the bone defect.

According to another aspect of the present invention, the implant is resorbable. The resorption of the implant, according to the present invention, can prevent stress shielding of the bone defect, to thereby prevent resorption of new bone which would occur if the bone defect were stress shielded by either the fixation device or the implant, or both. The fixation device may be resorbable or non-resorbable. When the fixation device is resorbable, the fixation device loses its mechanical strength within 24 months and, more preferably, within 4 to 12 months. This loss of mechanical strength of the fixation device can prevent resorption of new bone near the bone defect which would occur if the bone defect were stress shielded by either the fixation device, the implant, or both. If the fixation device is non-resorbable, according to the present invention, the resorption of the implant can reduce stress shielding of the bone defect area to thereby minimize resorption of new bone near the bone defect. As another option, the implant may be non-resorbable, but flexible enough to prevent stress shielding of the bone defect after the resorbable fixation device has lost its mechanical strength.

Each of the apertures within the implant has a diameter in a range between 20 microns and 3000 microns, and, preferably, has a diameter of approximately 1500 microns. The implant has a thickness in a range between 100 microns and 2000 microns, but may also be configured as thin as 10 microns. This implant comprises at least one of a biodegradable synthetic material and a biodegradable natural material, that is also a non-osteogenic, non-metallic substance having a stiffness sufficient to prevent gross soft tissue prolapse into an area of the bone defect where new bone ideally would grow.

According to one aspect of the present invention, a planar membrane is provided for preventing soft tissue from prolapsing into a protected area of a bone defect. The planar membrane is adapted for being placed outside of the bone defect area, as opposed to being placed within the bone defect area where new bone would ideally grow, to thereby facilitate entirely new bone growth only within the protected area. The planar membrane includes a plurality of apertures disposed therein. Each of the plurality of apertures is adapted for allowing a proliferation of vasculature and connective tissue cells into the protected area, while preventing a prolapse of adjacent soft tissues into the protected area. The planar membrane is adapted for resorption into the body of a patient, within a period of approximately 24 months from an initial implantation of the planar membrane into the body of the patient.

According to another aspect of the present invention, a resorbable membrane is provided for facilitating protected bone regeneration. The resorbable membrane is adapted for being wrapped around the bone defect area, to thereby cover and surround the entire bone defect area and to overlap adjacent areas of bone near the bone defect area. The resorbable membrane has a strength sufficient to prevent prolapse of adjacent soft tissues into the bone defect area and to thereby facilitate bone regeneration independently, without any aid from a fixation device, when the resorbable membrane is secured around the bone defect area and secured to the adjacent areas of bone near the bone defect area. The resorbable membrane forms a tube surrounding the entire bone defect area and overlapping the adjacent areas of bone near the bone defect area, when the resorbable membrane is secured both around the bone defect area and to the adjacent areas of bone near the bone defect area. The resorbable membrane can be frictionally secured around the bone defect area, or can be secured around the bone defect area using at least one of clamps, staples, screws, sutures, and tacks. The fixation device can include at least one of a plate, a screw, an intramedullary rod, and an external fixation device.

According to yet another aspect of the present invention, a method of protecting a biological tissue defect area from soft tissue interposition is provided. The method includes a step of placing a resorbable membrane outside of a boundary of the biological tissue defect, where the resorbable membrane comprises a plurality of apertures adapted for allowing a proliferation of vasculature and connective tissue cells therethrough, while preventing the prolapse of adjacent soft tissues into the biological tissue defect. The biological tissue defect area can include a bone defect area, and the step of placing a resorbable membrane outside of the boundary of the bone defect area can include a step of wrapping the resorbable membrane around two ends of a long bone to thereby surround a void between the two ends of the long bone. A rigid fixation device can subsequently be secured between the two ends of the long bone.

The present invention, together with additional features and advantages thereof, may best be understood by reference to the following description taken in connection with the accompanying illustrative drawings.

DETAILED DESCRIPTION OF THE PRESENTLY PREFERRED EMBODIMENTS

Figure 2:
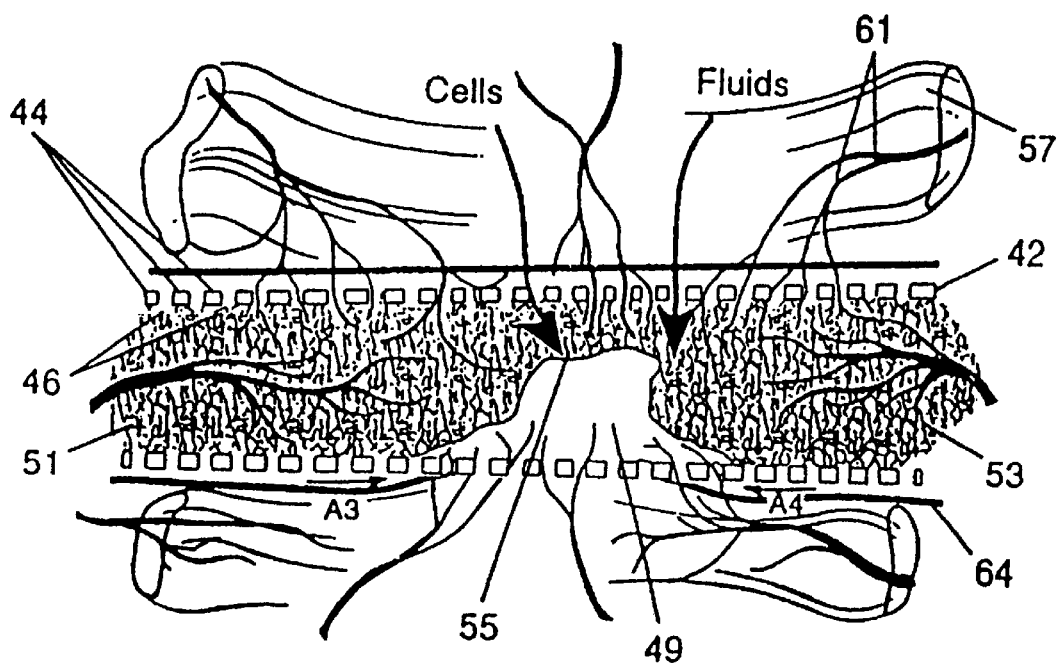
FIG. 2 illustrates a longitudinal cross-section of the protective bone regeneration membrane secured around a long bone defect according to the presently preferred embodiment.

Turning to FIG. 2, a protective bone regeneration membrane 42 is illustrated, comprising a base material 44 and apertures 46. The protective bone regeneration membrane 42 is shown in FIG. 2 wrapped around a bone defect area 49. The bone, which is surrounded by the protective bone regeneration membrane 42, comprises a first section of long bone 51, a second section of long bone 53, and a partially healed intermediate section of long bone 55. The protective bone regeneration membrane 42 is rigid enough to prevent prolapse of the surrounding tissues 57 into the bone defect area 49. Additionally, the apertures 46 of the protective bone regeneration membrane 42 are large enough to allow for a proliferation of blood vessels 61 therethrough and into the first section of long bone 51, the second section of long bone 53, and the partially healed bone defect 49. Since the protective bone regeneration membrane 42 of the presently preferred embodiment is rigid enough to withstand prolapse of the surrounding tissue 57, the regeneration of the partially damaged periosteum 64 is guided over the protective bone regeneration membrane 42 in a direction substantially parallel to the arrows A3 and A4.

Figure 1:
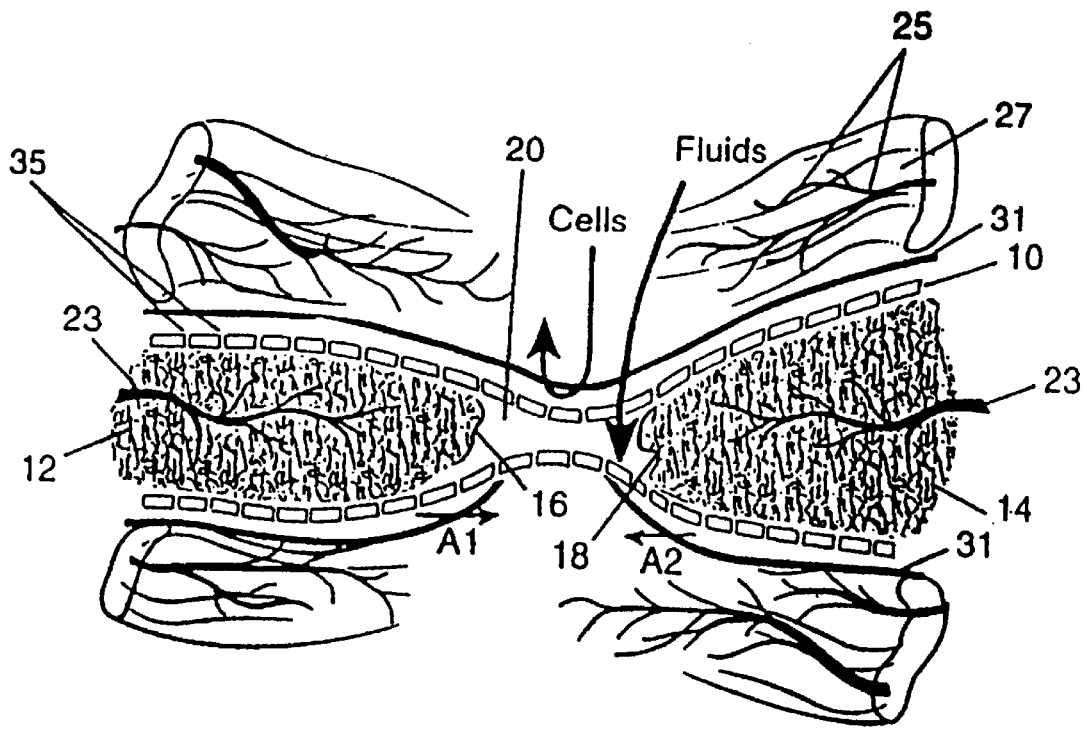
FIG. 1 illustrates a longitudinal cross-section of a cell-occlusive membrane secured around a long bone defect according to the prior art.

The apertures 46 within the protective bone regeneration membrane 42 are both cell and fluid permeable, and the base material 44 of the protective bone regeneration membrane 42 is rigid enough to maintain the available space between the first section of long bone 51 and the second section of long bone 53 for ideal bone regeneration. Additionally, the base material 44 is resorbable, according to the presently preferred embodiment. The cell-occlusive membrane of the prior art membrane 10 (FIG. 1), in contrast, is specifically designed to prevent the proliferation of cells and vessels therethrough. This membrane 10 is also insufficiently rigid and non-resorbable.

Figure 3A:
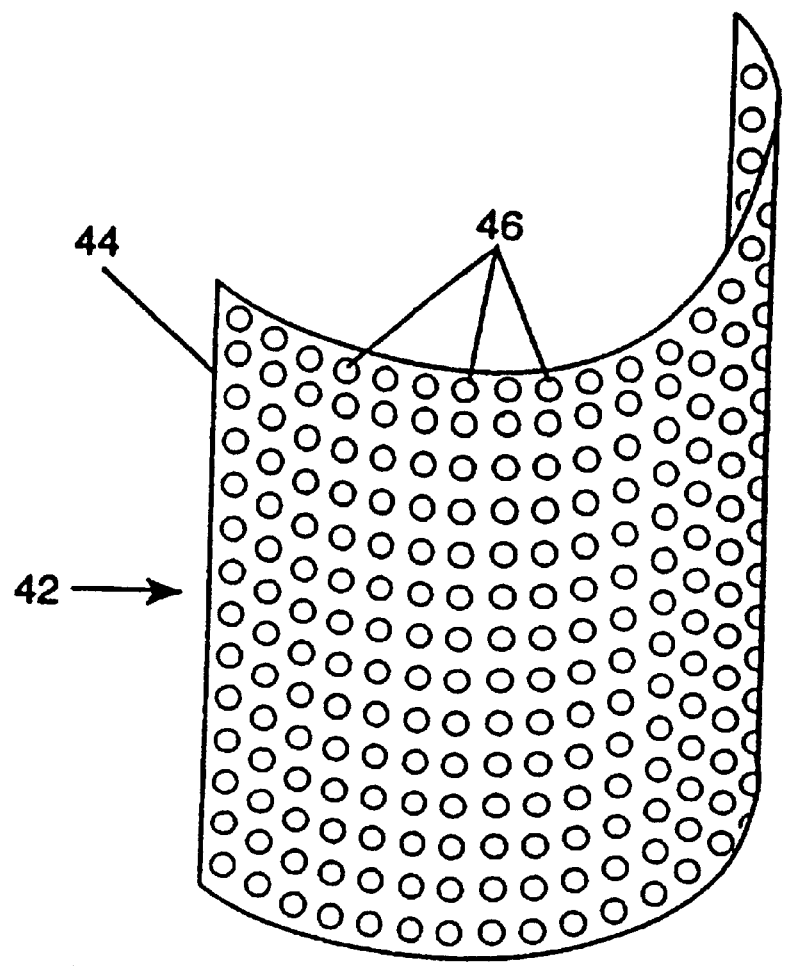
FIGS. 3a and 3b illustrate the protective bone regeneration membrane according to the presently preferred embodiment.
Figure 3B:
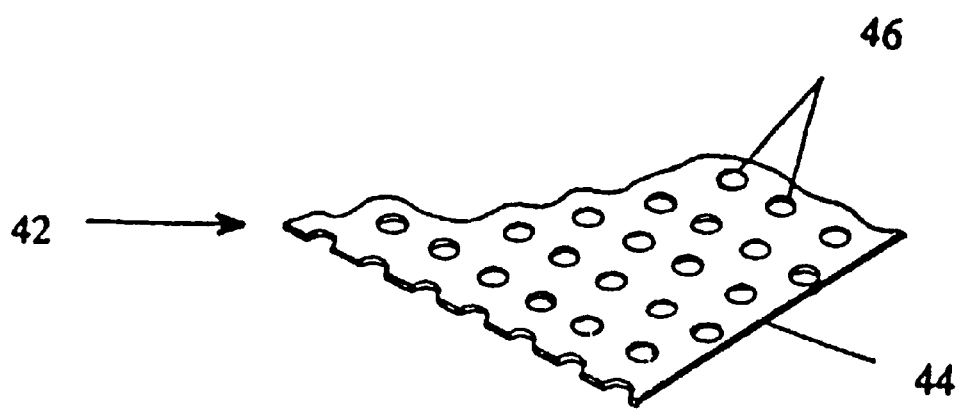

FIGS. 3a and 3b illustrate different embodiments of a sheet of the protective bone regeneration membrane 42, comprising the base material 44 and the apertures 46. As presently embodied, the protective bone regeneration membrane 42 comprises either a biodegradable synthetic material or a biodegradable natural material, or both. The biodegradable synthetic material may comprise polymers, for example, and the biodegradable natural material may comprise collagen, for example. Each of the apertures 46 preferably has a diameter within a range of between 20 microns and 3000 microns. In the presently preferred embodiment, each aperture 46 comprises a diameter of approximately 1500 microns. A thickness of the base material 44 is preferably within a range between 100 microns and 2000 microns, but may also be configured as thin as 10 microns. The pattern of distribution of the apertures 46 may vary according to the bone defect being treated. The ranges of aperture 46 sizes, base material 44 thickness, and aperture 46 shape and distribution is preferably implemented by the present invention in order to optimize the protective bone regeneration membrane 42 to different environmental conditions. Examples of the different environmental conditions encountered in different bone defects include the location of the defect (long bone or flat bone), the type of defect (discontinuity defect, contour defect, window defect, trephine defect), size of the defect, the presence or absence of periosteum 64, and the general condition of the adjacent soft tissues covering the bone defect.

Figure 4:
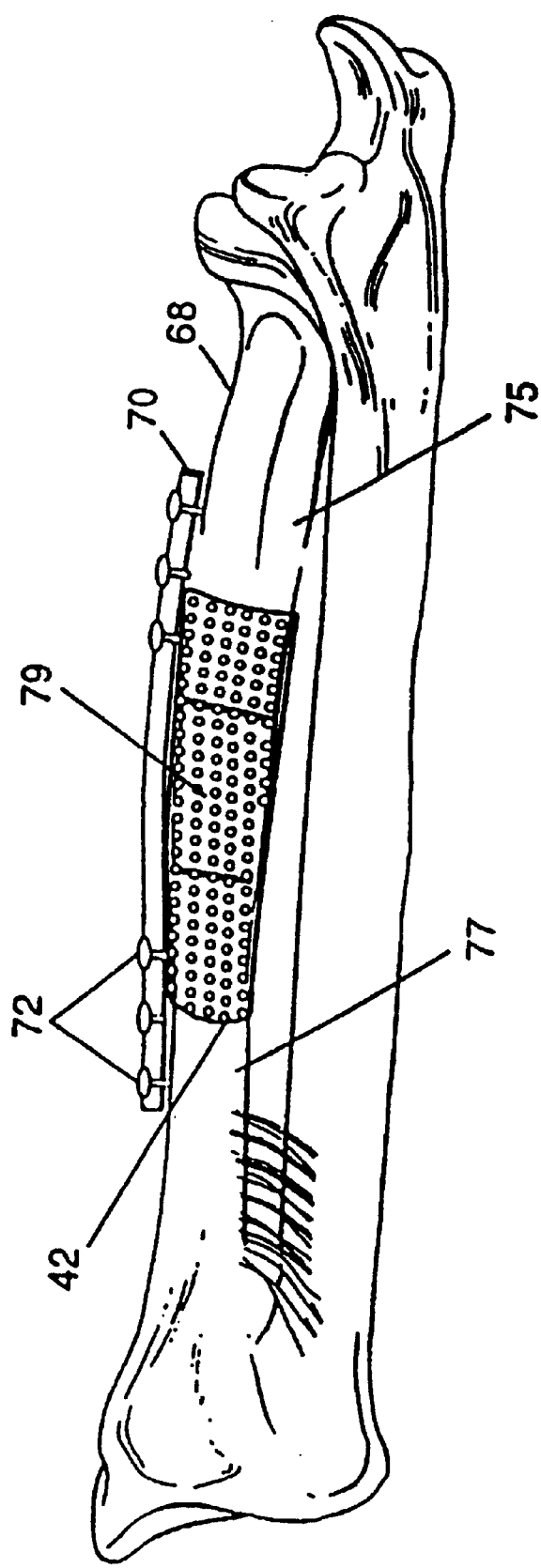
FIG. 4 illustrates the protective bone regeneration membrane of the present invention, as applied to a long bone defect.

FIG. 4 illustrates the protective bone regeneration membrane 42 applied to a long bone 68 of a patient. The protective bone regeneration membrane 42 is applied to the long bone 68 in combination with a fixation device 70. The fixation device 70 can be secured to the long bone 68 using conventional means, such as tacks or screws 72.

The fixation device 70, the screws 72, and the protective bone regeneration membrane 42 together securely hold the first section 75 of the long bone 68 to the second section 77 of long bone 68. A bone defect area 79 is protected against the prolapse of adjacent soft tissues, for example, by the protective bone regeneration membrane 42.

In contrast to the titanium screen mesh of the prior art, the inventors believe that the combination of the protective bone regeneration membrane 42 and the fixation device 70 may in some instances be adapted for operating together to relieve stress shielding of the long bone 68, to thereby prevent subsequent resorption of new bone. The prior art titanium screen mesh is designed to remain permanently attached to the bone, resulting in long-term stress shielding and resorption of newly formed bone within the bone defect area 79. In contrast to the prior art titanium screen mesh, the protective bone regeneration membrane 42 of the present invention is preferably configured of a resorbable, bio-compatible material. At about the time that the new bone within the bone defect area 79 is fully regenerated, the protective bone regeneration membrane 42 of the presently preferred embodiment will have resorbed sufficiently to no longer shield stress from the bone defect area 79 to thereby encourage an increase of bone formation. In addition, according to the presently preferred embodiment, the fixation device 70, and/or the screws 72, are also formed of a resorbable material. That is, the combination of the fixation device 70, the screws 72, and the protective bone regeneration membrane 42 prevent excessive motion between the first section 75 and the second section 77 of the long bone 68.

As presently embodied, this period of time sufficient for complete new bone regeneration within the bone defect area 79 is between approximately 2 to 24 months. Thus, according to the present invention, the resorption of the protective bone regeneration membrane 42 to a point where the protective bone regeneration membrane 42 can no longer shield significant mechanical stress on the first section 75 and the second section 77 is between approximately 2 and 24 months.

In an alternative embodiment, the protective bone regeneration membrane 42 may comprise a non-resorbable material. In this alternative embodiment where the protective bone regeneration membrane 42 is non-resorbable and the fixation device 70 is resorbable, resorption of newly formed bone within the bone defect area 79 is still prevented. More particularly, the protective bone regeneration membrane 42 is configured to be flexible enough to prevent stress shielding between the first section 75 and the second section 77, after the fixation device 70 has been resorbed to a point where the fixation device 70 no longer exerts mechanical strength on the first section 75 and the second section 77 of the long bone 68.

As another distinguishing feature, the protective bone regeneration membrane 42 of the present invention is designed to be used in combination with a fixation device 70, in a preferred embodiment, while the titanium screen mesh of the prior art comprises a fixation device designed predominantly to be used alone. In one conceivable embodiment of the present invention, the protective bone regeneration membrane 42 of the present invention may be used in combination with the prior art titanium screen mesh, as well as in combination with any other conventional fixation device. Generally, internal fixation devices can be divided into two classes. Cortical compression plates comprise a first class and intramedullary rods comprise a second class. Both classes of devices are unable to secure and stabilize shattered bone, because bone fragments are often small and free floating within the fracture cavity. Furthermore, the periosteum around such fracture sites is usually destroyed and cannot serve as a membrane barrier against the dislocation of bone fragments. Multiple bone fragments are naturally resorbed unless they can be rigidly held together and provided with sufficient blood supply. Bone fragment resorption can present a significant obstacle to efficient healing of comminuted fractures. Bone fragment resorption often necessitates additional bone grafting procedures. In contrast to the protective bone regeneration membrane 42 of the present invention, both of the above mentioned classifications of fixation devices are unable to achieve this end.

The protective bone regeneration membrane 42 of the presently preferred embodiment is preferably resorbed within the body of the patient to a point where substantial mechanical fixation is no longer exerted on the first section 75 and the second section 77 of the long bone 68, within a period of approximately 1 year. Complete resorption of the protective bone regeneration membrane 42 may subsequently occur after a total period of 1½ to 2 years have elapsed since the initial implantation. In contrast to the allogenic bone grafts of the prior art, the protective bone regeneration membrane 42 of the present invention is resorbed into the body of the patient. Allogenic bone grafts are only partially substituted with new bone over time, typically comprising 1 to 2 years, forming a permanent composite of viable (new) bone and non-viable cadaver bone. Thus, allogenic bone grafts cannot achieve a complete regeneration of the entire bone defect with new living bone, as can the protective bone regeneration membrane 42 of the present invention. This benefit is achieved by placement of the protective bone regeneration membrane 42 outside of the bone defect area 49, rather than within the bone defect area 49. Additionally, the holes within the allogenic bone graft of the prior art are substantially occluded by induced bone formation therein within approximately 2 to 3 weeks after the initial implantation. Finally, as a further distinguishing feature between the protective bone regeneration membrane 42 of the present invention and the prior art allogenic bone graft, the prior art allogenic bone graft is placed within the bone defect area itself, since the purpose of the prior art allogenic bone graft 42 is to become a part of the new bone. In contrast, the protective bone regeneration membrane 42 of the present invention is designed to be placed completely outside of the bone defect area, in order to maintain a maximal size of the bone defect area 79 for regeneration of new bone by the patient in the area 79. Still further, allogenic bone grafts are inferior to the protective bone regeneration membrane 42 of the present invention in providing a combination of patient safety in preventing disease transmission, optimal prolapse prevention and maximal space preservation for bone regeneration, and vasculature ingrowth potential. Similarly to the allogenic bone graft of the prior art, the above-mentioned skin graft. of the prior art comprises apertures which are quickly occluded by the ingrowth of epithelial cells therein. These prior art apertures, similarly to the allogenic bone graft holes, are actually filled with the desired tissues, whereas, the apertures of the protective bone regeneration membrane 42 allow ongoing transmigration of cells and blood vessels for generating the desired tissue. Additionally, these apertures are formed having a diameter of approximately 1 millimeter, whereas the preferred diameter of the apertures of the present invention are approximately 1.5 millimeters. Additionally, the skin graft membrane of the prior art is specifically designed for providing an in vitro scaffold and subsequent transplantable skin graft, whereas the present invention preferably operates in vivo.

Many of the above-described differences between the protective bone regeneration membrane 42 of the present invention and prior art devices help point to a fundamental difference between the present invention and prior art devices. The present invention is directed to maintaining a space, protected against adjacent soft tissue prolapse, to thereby facilitate spontaneous bone regeneration by the patient within the protected space. The present invention recognizes that spontaneous bone regeneration by the patient can be greatly accelerated and enhanced by allowing the infiltration of surrounding blood vessels and cells.

The present inventors recognize that mesenchymal stem cells, which can be found in surrounding mesodermal tissues, are the precursor cells that eventually form muscle, cartilage, tendons, ligaments, connective tissues, and bone. These cells are present in these tissues and are involved in the perpetual renewal of each specific tissue, although in their earliest stage development, these cells are not committed to becoming any given tissue. An uncommitted mesenchymal stem cell found in muscle, for example, will not strictly become a muscle cell. If the mesenchymal stem cell is needed to become a bone cell, the mesenchymal stem cell may migrate to a bone defect and differentiate into a bone forming cell. The mechanism for attracting these cells and directing them to become a specific tissue cell is understood by the present inventors to be controlled by morphogenic proteins, although other factors may be involved. In bone, for example, these proteins are commonly referred to as bone morphogenic proteins. The apertures 46 of the protective bone regeneration membrane 42 harness this mechanism, by allowing bone morphogenic proteins derived from within the bone matrix to attract mesenchymal stem cells from the surrounding connective tissues, musculature, periosteum, and vasculature. The attracted elements are then directed to differentiate into bone forming cells, which are essential for new bone formation by the patient. In addition, the apertures 46 of the present invention allow vital contributions of blood vessels from surrounding tissues, musculature, and periosteum into the protected area. Blood vessels invading the bone defect through the protective bone regeneration membrane 42 of the present invention greatly enhance the generation of new bone, as compared to prior art cell-occlusive membranes that limit the supply of blood to that coming from within the bone defect itself. The ability for capillaries from surrounding soft tissues to proliferate through the protective bone regeneration membrane 42 helps prevent migrating cells from the osseous bed and the periosteum from outstripping their proliferating blood supply. This proliferation of blood vessels increases the potential of spontaneous bone regeneration within a given defect. Furthermore, mesenchymal stem cells are believed to be perivascular (around blood vessels) connective tissue cells, which would additionally foster bone regeneration by the transmembranous sprouting of capillaries, since most vasculature has associated connective tissues.

The base material 44 (FIG. 3), according to the present invention, may be impregnated with a variety of substances for promoting the regeneration of different tissues such as bone and blood vessels. The base material 44 may be impregnated with a chemotactic substance for influencing cell-migration, an inhibitory substance for influencing cell-migration, a mitogenic growth factor for influencing cell proliferation and a growth factor for influencing cell differentiation (e.g. insulinelike growth factor, transforming growth factor-beta, fibroblast growth factor, platelet-derived growth factor), and factors which promote neoangiogenesis (formation of new blood vessels).

According to the present invention, the base material 44 is flexible both at the time of manufacture and after hydration. This flexibility allows the protective bone regeneration membrane 42 to be bent and shaped such that, after the area is completely healed, the contour of the healed bone matches the contour of the original bone, or matches the contour of the original bone as closely as possible. According to the present invention, the base material 44 (FIG. 3) further provides an advantageous rigidity, which is higher than other currently used membrane materials (FIG. 1) to thereby provide sufficient strength against soft tissue pressure.

The method of the present invention generally comprises a step of affixing the protective bone regeneration membrane 42 (FIG. 3) onto a portion of the mammalian skeletal system in need of repair. The fixation of the protective bone regeneration membrane 42 may be accomplished by any conventional surgical technique, including the use of resorbable pins, screws, and sutures. Alternatively, the protective bone regeneration membrane 42 of the present invention can be implanted into the patient without being affixed to existing bone, such as, for example, in the case of orbital floor reconstruction 84 (FIG. 5).

Figure 5:
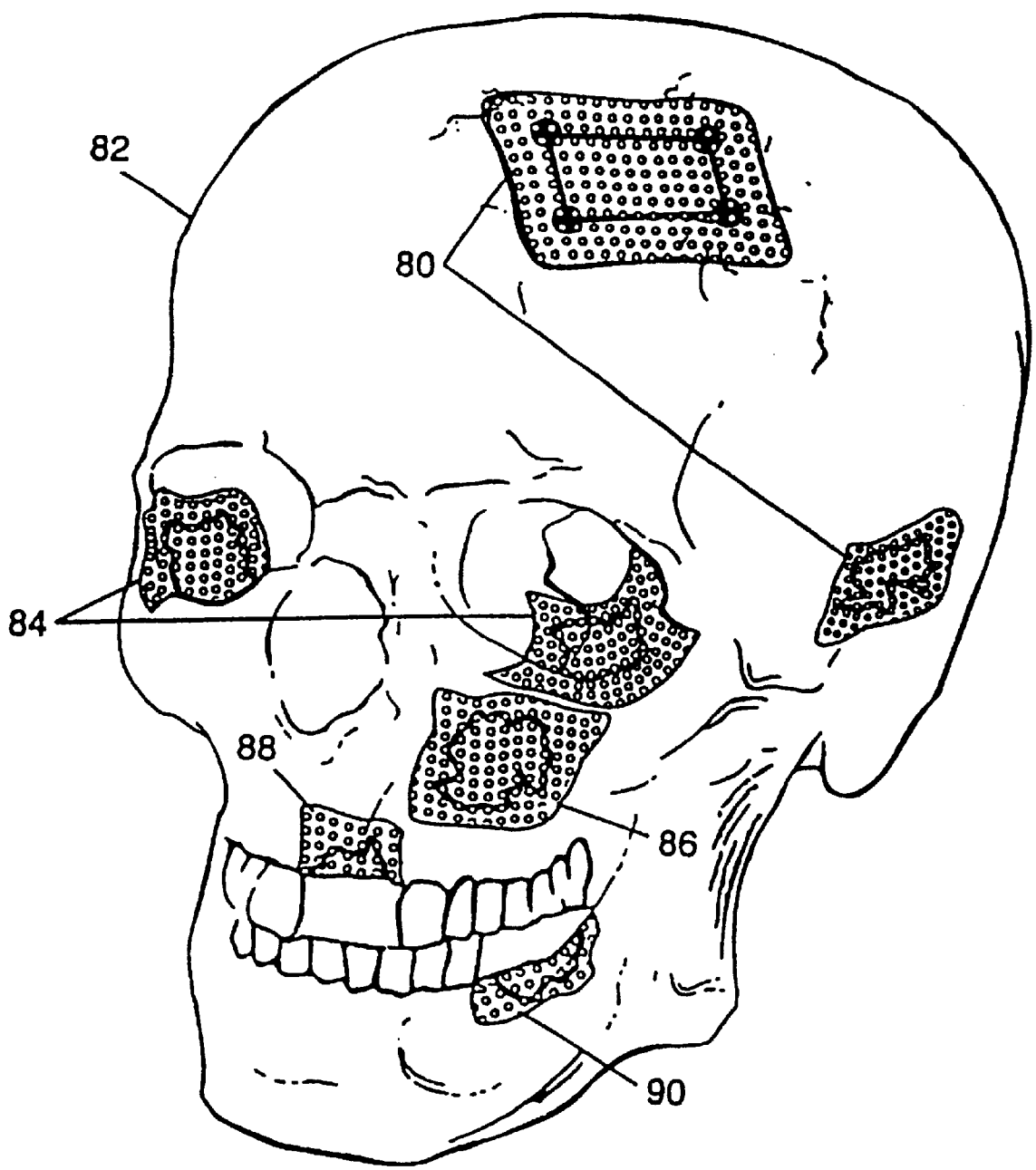
FIG. 5 illustrates the protective bone regeneration membrane of the present invention, applied to various bone defect areas of a human skull.

Other applications of the protective bone regeneration membrane of the present invention are illustrated in FIGS. 5–8. FIG. 5 illustrates several applications of the protective bone regeneration membrane in the cranio-facial region of a human skull. A protective bone regeneration membrane 80 is applied over the burrholes and the trephination defect of a human skull 82, after a neurosurgical procedure or trauma. Inside the orbits of the skull, protective bone regeneration membranes 84 are placed over orbital floor fractures to prevent entrapment of overlying muscles and nerves therein. Another protective bone regeneration membrane 86 is applied over a defect area in the maxillary sinus, and still another protective bone regeneration membrane 88 is applied over a bone defect area in the maxilla (upper jaw). Another protective bone regeneration membrane 90 is applied over an edentulous bone defect area in the mandible (lower jaw).

Figure 6:
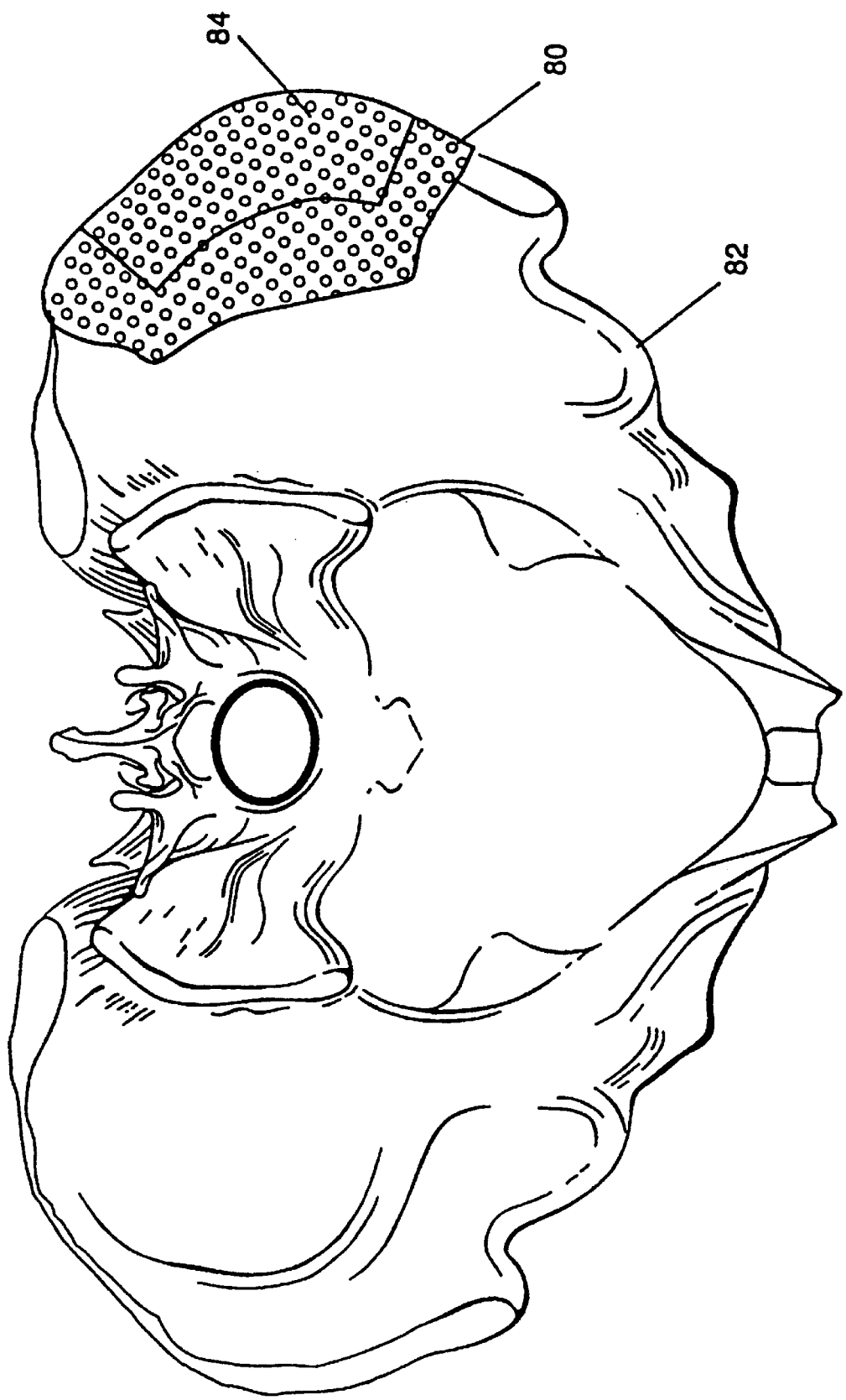
FIG. 6 illustrates the protective bone regeneration membrane of the presently preferred embodiment, used to facilitate bone regeneration of the iliac crest of a patient, after a bone autograft has been harvested from the patient.
Figure 7:
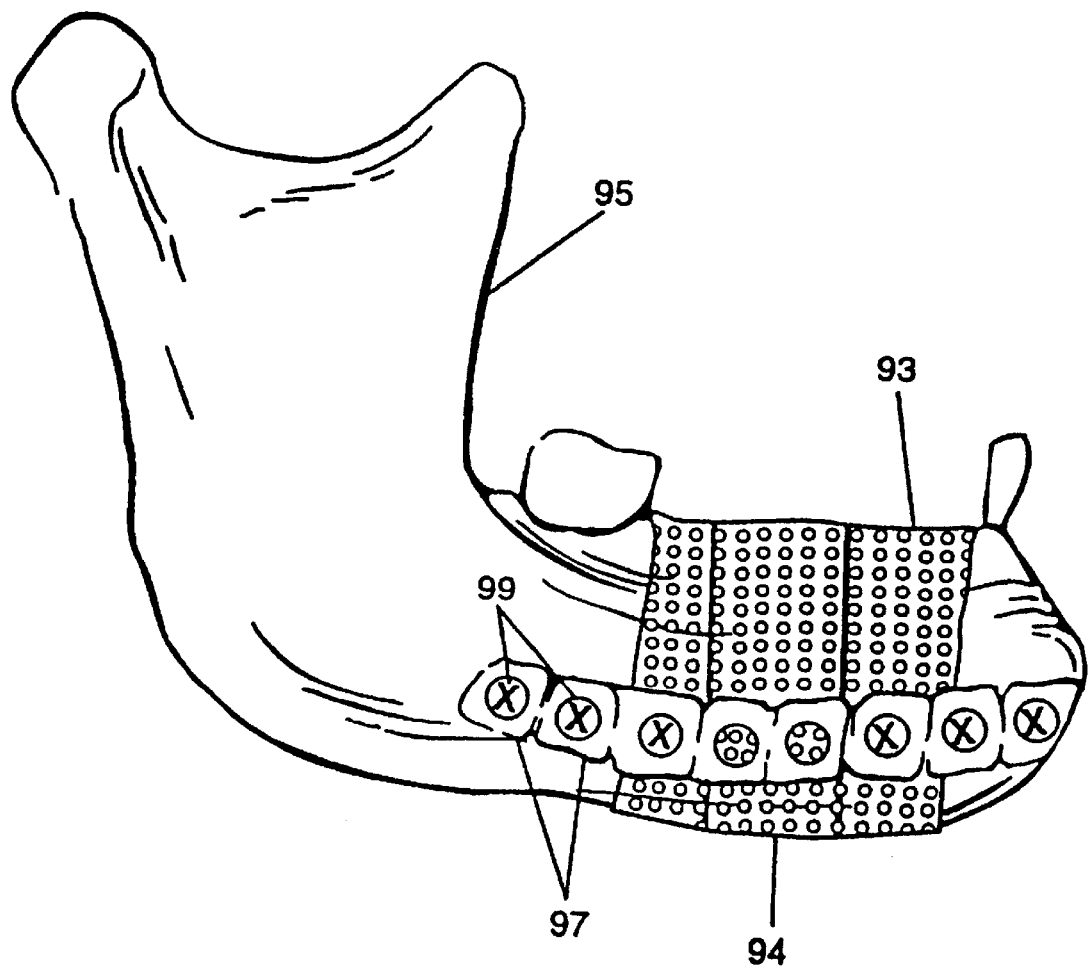
FIG. 7 illustrates the protective bone regeneration membrane of the present invention, as applied to a mandibular (lower jaw) bone defect of a patient.

A protective bone regeneration membrane 80 is illustrated in FIG. 6, applied to the pelvis 82 of a human patient, after a bone autograft has been harvested therefrom. The protective bone regeneration membrane 80 protects the bone defect area 84 from soft tissue interposition, while allowing the ingrowth of blood vessels and cells. If necessary, the protective bone regeneration membrane 80 can be affixed onto the adjacent bone using pins, screws, sutures, or other conventional means. FIG. 7 illustrates a protective bone regeneration membrane 93 applied around a segmental defect 94 in a human mandible 95, for example. The protective bone regeneration membrane 93 can be implanted using an extra-oral (outside of the mouth) surgical approach. According to this approach, the epithelial lining of the mouth is not broken and the protective membrane is placed beneath the epithelial lining of the mouth (since the bone defect is accessed from an extra-oral area such as below the chin). Therefore the epithelial cells cannot enter the bone defect. The present invention, however, is also intended to apply in intra-oral surgical approaches. The defect may be a discontinuity defect, comminuted, or just missing a part of the bone. The intact parts of the mandible 95 are fixated together by a plate 97 and screws 99, if necessary, and the protective bone regeneration membrane 93 protects the bone defect site from interposition of surrounding soft tissue. Additionally, the protective bone regeneration membrane 93 holds any free-floating fragments of bone in place and provides additional circumferential stabilization to the bone defect. Although the protective bone regeneration membrane 42 is malleable to a certain extent, the protective bone regeneration membrane 42 is stiff enough to prevent collapse thereof under the weight of adjacent soft tissues. The protective bone regeneration membrane 42 can be easily cut with scissors and shaped by the hand of a user to adapt three-dimensionally to a bone defect area.

Figure 8:
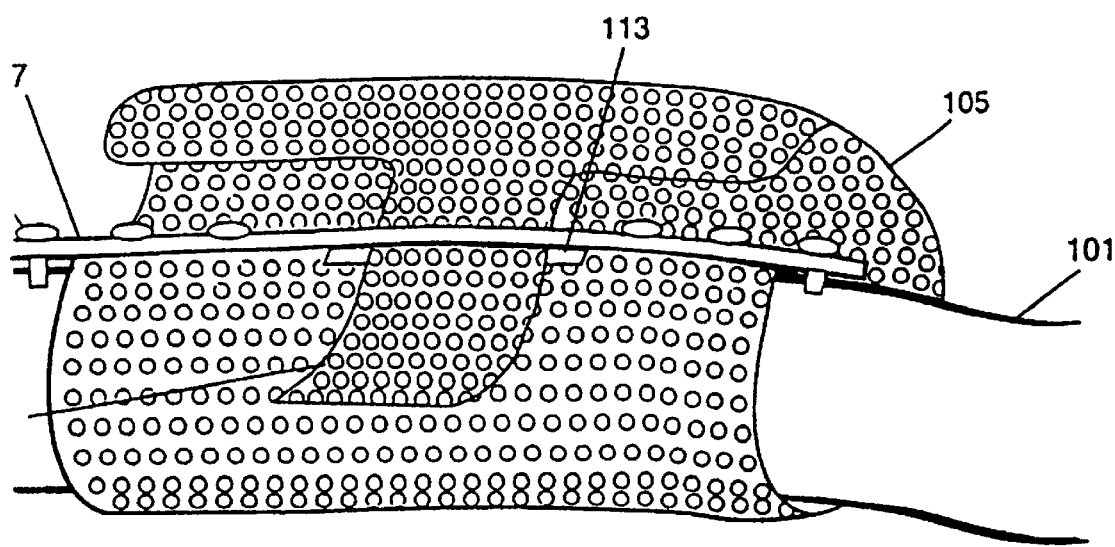
FIG. 8 illustrates the protective bone regeneration membrane of the present invention, used in combination with a fixation device, as applied to a long bone defect of a patient.

FIG. 8 illustrates another application of the protective bone regeneration membrane 105 of the present invention, as applied to a bone defect area of a long bone 101. The protective bone regeneration membrane 105 is secured to the long bone 101 using fixation devices 107 and 109, and comprises a belt-like tab 111. The belt-like tab 111 is adapted for being fed through a slot 113, which is formed between the fixation member 107 and the long bone 101. In the presently preferred embodiment, the protective bone regeneration membrane 105 is secured to the fixation member 107, and both the protective bone regeneration membrane 105 and the fixation member 107 are resorbable, in order to avoid a second surgery for removal of the devices. Surgical removal of non-resorbable, non-metallic membranes is necessary in the prior art, in order to avoid risk such as bacterial contamination and infection. A user can grip the belt-like tab 111 to securely fasten the protective bone regeneration membrane 105 around the long bone 101. This secure fastening of the protective membrane 105 around the long bone 101 can facilitate the holding of bone fragments in place within the bone defect area, in addition to adding stability to the bone fracture. In the presently preferred embodiment, the screws 109 are tightened into the long bone 101 after the protective bone regeneration membrane 105 is tightened around the long bone 101. The embodiment of FIG. 8 is especially advantageous for setting comminuted fractures, having multiple bone fragments, to thereby reduce the risk of bone fragment resorption. The protective bone regeneration membrane 105 can be tightened around the long bone 101, until a desired tension is achieved for holding the native fracture fragments in place. The protective bone regeneration membrane 105 can also be used to prevent the dislocation of bone grafts or bone graft substitutes. Of course, the protective bone regeneration membrane 105 may be used without a fixation device 107. If it is necessary to stabilize major bone fragments, the protective bone regeneration membrane 105 may be used in conjunction with other rigid fixation devices, either internal or external.

The protective bone regeneration membrane 105 may be used with or without a belt-like tab 111 to form a tube around a bone defect area of a long bone 101. If the tube overlaps both fracture ends of the long bone 101, the tube may provide sufficient structural support, resulting from the strength of the protective bone regeneration membrane 105 and the structural characteristics of the tube, to obviate the need for additional plates, screws, or external fixation devices. Structurally, a tube locates supporting elements in the area of highest stress when loaded in shear, compression, or in bending. The tube configuration, according to this alternative embodiment, is superior to intramedullary rods, which lay at the approximate neutral load axis, or eccentrically placed orthopedic plates, which support only one side of the fracture and which may introduce asymmetrical, non-axial loading on the fracture. In addition to superior strength in bending, a tube configuration will also have superior resistance to column (compression) loading. If the ends and seam of the protective bone regeneration membrane 105 are suitably fixated, the configuration will also be superior in shear strength. Although the present material, configurations, and methods have been described in the context of treating humans, these materials, configurations, and methods can also be useful in treating animals.

FIGS. 9–13 disclose a number of embodiments of the resorbable sheet in accordance with different aspects of the present invention. The resorbable sheet of the present invention is preferably thermoplastic (thermally-pliable). In one embodiment, the membrane can be shaped around a biological tissue defect at temperatures in a range of 55–60 degrees Celsius (glass transition temperature).

One important concept of the present invention is the addition of what will be referred to as "tissue guiding agents" to the resorbable sheet.

Another inventive feature of the present invention includes the addition of what will be referred to as "membrane strengthening agents" to the resorbable sheet.

The membrane strengthening agents may be separate from, or integral with, the tissue guiding agents. The construction of the resorbable sheet, in accordance with the present invention, does not necessarily depend on any particular membrane thickness or pore size of the resorbable sheet, so long as the membrane thickness and the pore size are proportionately sized and configured to accommodate the membrane strengthening agents and/or the tissue guiding agents.

In accordance with one embodiment of the present invention, the tissue guiding agents are preferably disposed on the interior surface of the resorbable sheet along one or more directions, facing the biological tissue defect. The directions may be parallel or nonparallel to one another.

The tissue guiding agents, in accordance with one embodiment of the present invention, comprise parallel corrugations on the interior surface of the resorbable sheet. The corrugations are directed along an axis (or axes) which is (are) parallel to the desired direction(s) of growth of the tissue to be regenerated. For example, in a case where the resorbable sheet is wrapped around a long bone (see FIG. 4), the corrugations preferably extend along the interior surface of the resorbable sheet in a direction generally parallel to a longitudinal axis of the long bone.

In another embodiment, such as, for example, in a case where the resorbable sheet is placed over a biological tissue defect (see FIG. 5), the corrugations preferably extend on the interior surface of the resorbable sheet in a radially inward direction toward a center of the resorbable sheet. The corrugations, alternatively, may all be parallel to one another. In accordance with the present invention, the radially inwardly extending corrugations help to facilitate (guide) newly generated tissue in a direction toward a center of the bone defect area (e.g., cranial bone defects, for example). The radially inwardly extending corrugations may comprise a plurality of nonparallel corrugations radially extending from a center of the resorbable sheet, or, as another example, may comprise a plurality of perpendicular corrugations which generally extend from a center of the resorbable sheet in a radially outwardly direction.

Figure 10:
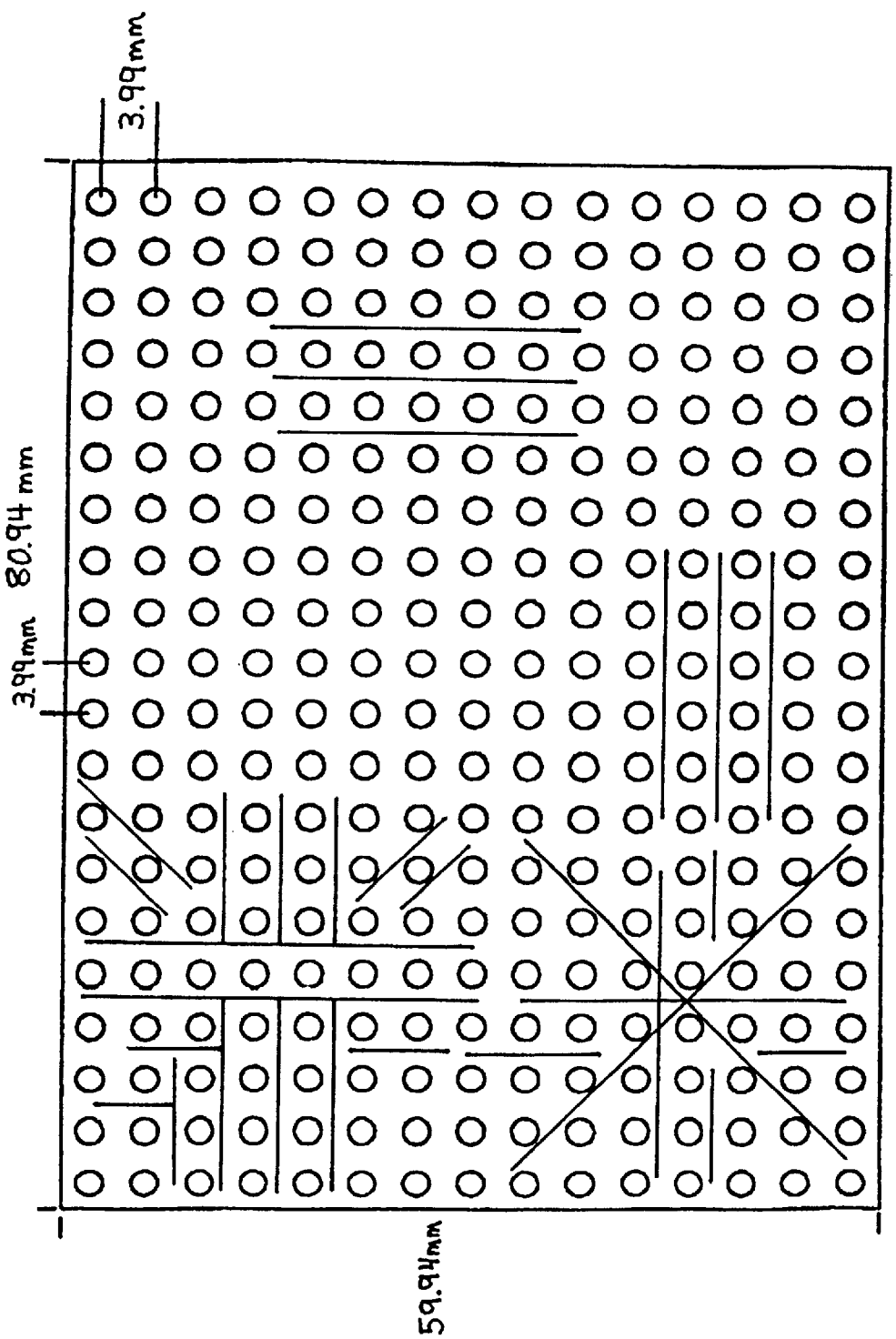

The upper left corner of FIG. 10 illustrates a plurality of radially extending, generally perpendicular corrugations disposed on a surface of a resorbable sheet. The corrugations are preferably continuous along a length and width of the entire resorbable sheet in order to provide additional strength to the resorbable sheet. Corrugations which do not extend along a length of the entire resorbable sheet, however, can still operate to provide tissue guiding functions along an interior surface of the resorbable sheet, for example. The upper left corner of FIG. 10 illustrates a number of various types of layouts of radially inwardly extending corrugations. Longitudinal and transverse corrugations may be used alone, or in combination with diagonally radially extending corrugations. Additionally, all, some, or none of the corrugations may extend along an entire length or width of the resorbable sheet. The lower left corner of FIG. 10 illustrates a plurality of radially extending corrugations which are not necessarily perpendicular. In this embodiment, a greater percentage, or all, of the corrugations may be configured to extend in a purely radial direction from a center of the resorbable sheet, or area of interest on the resorbable sheet.

The right side of FIG. 10 illustrates a plurality of corrugations extending parallel to one another along a length, for example, of the resorbable sheet. The middle portion of FIG. 10 illustrates a plurality of corrugations extending parallel to one another along a width, for example, of the resorbable sheet.

Figure 9:
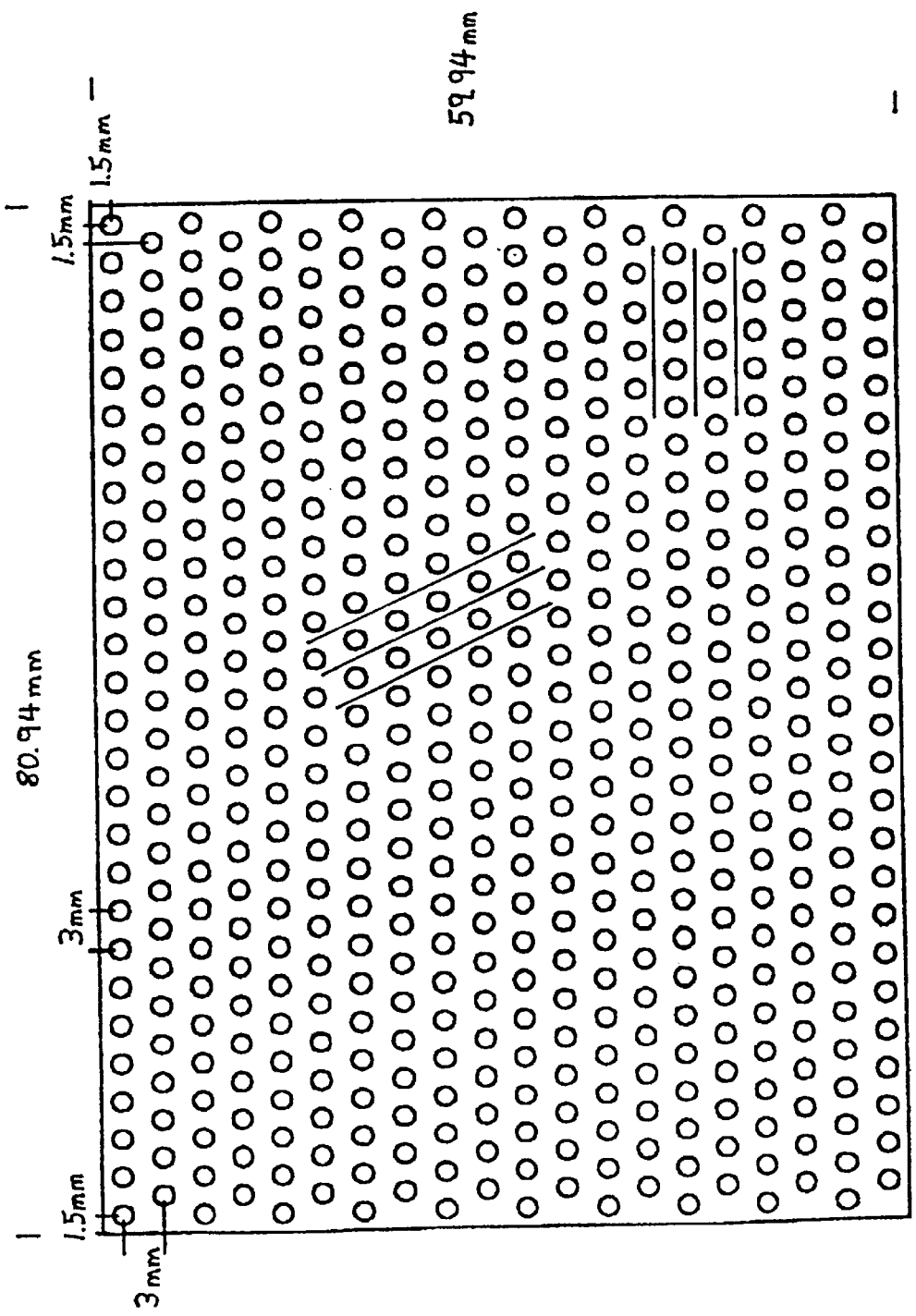
FIGS. 9–13 illustrate polymer sheets having tissue guiding and membrane strengthening agents.

Similarly, the right side of FIG. 9 illustrates a plurality of corrugations extending parallel to one another along a width, for example, of a resorbable sheet. The corrugations closer to the middle portion of FIG. 9 extend parallel to one another along another direction of the resorbable sheet. The diagonal direction may correspond (be oriented parallel with) to a lateral direction of the resorbable sheet or, alternatively, may correspond to a longitudinal direction of the resorbable sheet. In another alternative embodiment, the diagonally disposed corrugations may be aligned off-axes to both the longitudinal and lateral directions of the resorbable sheet.

Figure 11:
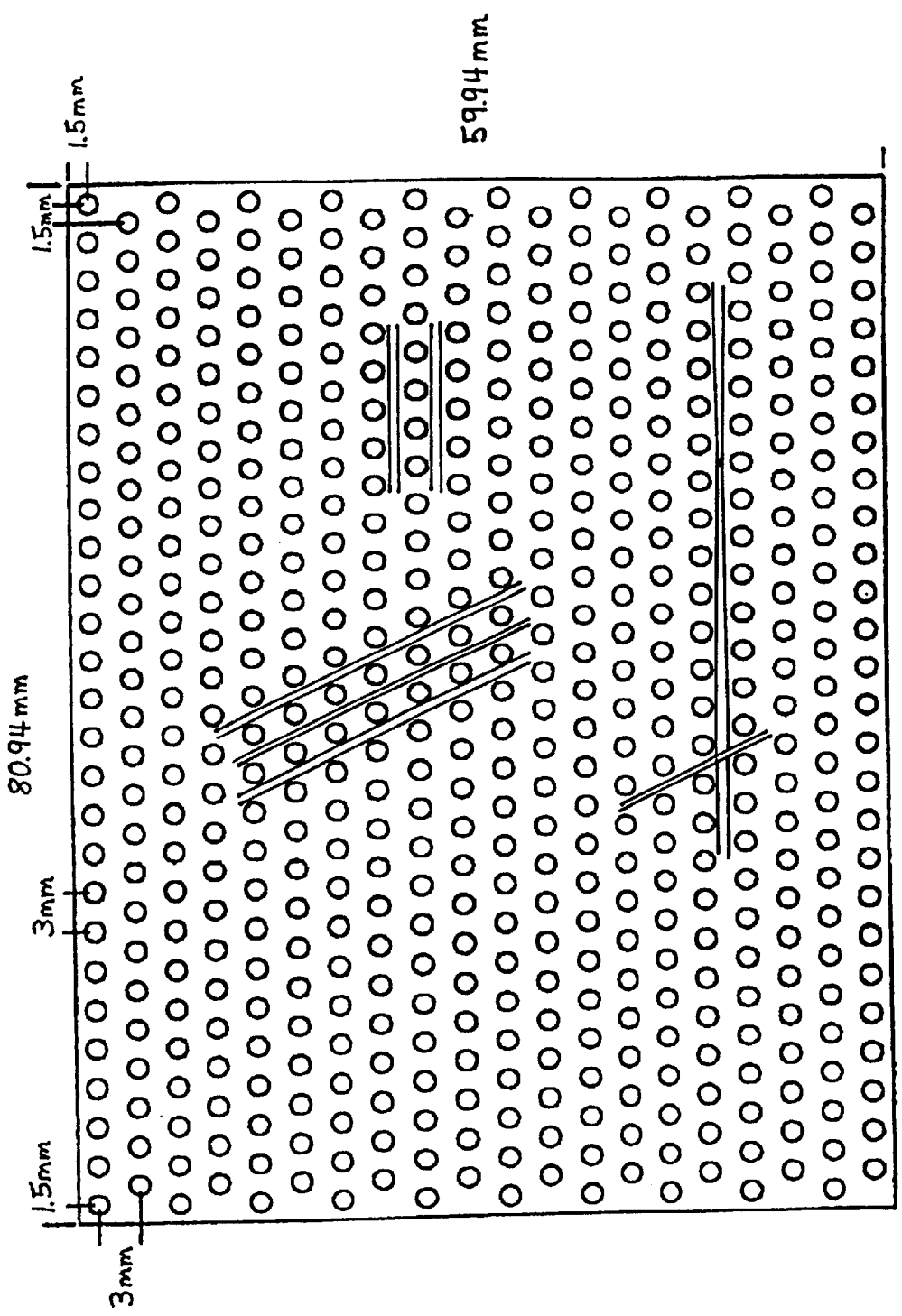

FIG. 11 illustrates additional configurations and embodiments of the corrugations of the present invention. The corrugations are illustrated in FIG. 11 having greater widths than those of FIGS. 9 and 10. The corrugations of FIG. 11 are shown extending in various directions and, in one place, intersecting one another. The widths of the corrugations may vary from a minimum width of approximately 5 microns to an unlimited maximum width. The maximum width of the corrugations of the present invention may even be greater than widths of the corresponding apertures, so that a given corrugation extends over one or more apertures. Alternatively, a width of the corrugations, in accordance with a present invention, can be much smaller than a width of an aperture, so that a plurality of corrugations can be disposed between any two or more apertures. Moreover, the width (and/or height) of a given corrugation may vary along a length of the corrugation, as illustrated, for example, in the lateral corrugation near the bottom portion of FIG. 11. This corrugation, moving from right to left in the figure, decreases in width and, subsequently, increases in width until the intersection with the diagonal line. The corrugation continues after the intersection with the diagonal line at a lesser width. Other patterns of varying widths, either continuous or discontinuous, are contemplated by the present invention. Such patterns may include, for example, geometrical shapes including triangles, rectangles or circles, disposed either between or over one or more apertures, for providing additional strength in certain areas. FIG. 11 illustrates a triangular area of increased thickness.

In addition to varying the orientation, width, height, and position, for example, relative to apertures of the resorbable sheet, the corrugations (tissue guiding agents) of the present invention can be configured as indents, for example, instead of protrusions on the surface of the resorbable sheet. In such an embodiment (having indents instead of protrusions on the surface), a thickness of the resorbable sheet outside of the tissue guiding agents may be greater than in other relative embodiments. Other embodiments are also possible, so long as a surface disturbance (tissue guiding agents) is introduced onto the formerly smooth surface of the resorbable sheet, on either one or both surfaces of the resorbable sheet.

In embodiments where the tissue guiding agents are not integral with (the same as, for example) the membrane strengthening agents, the membrane strengthening agents may be configured within the resorbable sheet. In such an embodiment, for example, the membrane strengthening agents do not disturb or alter the relatively smooth surface of the resorbable sheet. For example, a membrane strengthening agents may comprise a strengthening member or members disposed between the exterior and interior surfaces of the resorbable sheet. Any material, such as compounds, fibers, or other means may be used as strengthening members and placed within the base material of the resorbable sheet, either during or subsequent to an initial manufacturing step, and the resulting membrane strengthening agents may or may not extend to or disturb the surface (exterior or interior) of the resorbable sheet at all points or at any given point on the membrane.

The membrane strengthening agents are preferably resorbable. In one particular embodiment of the present invention, however, the membrane strengthening agents and/or the membrane itself (formerly referred to as the resorbable sheet) do not comprise a resorbable material. In yet another embodiment, the membrane strengthening agents may comprise aperture strengthening agents and/or membrane strengthening agents. In this embodiment, strengthening elements may be disposed around or in close proximity to apertures of the resorbable sheet for providing strength to the membrane.

In accordance with another embodiment of the present invention, tissue guiding agents (such as corrugations) and/or membrane strengthening agents may be disposed within apertures of the resorbable sheet, and/or in close proximity to the apertures. The tissue guiding agents comprise corrugations in a presently preferred embodiment, which are aligned to guide tissues, fluids, vasculature and cells into the apertures of the resorbable sheet.

Figure 12:
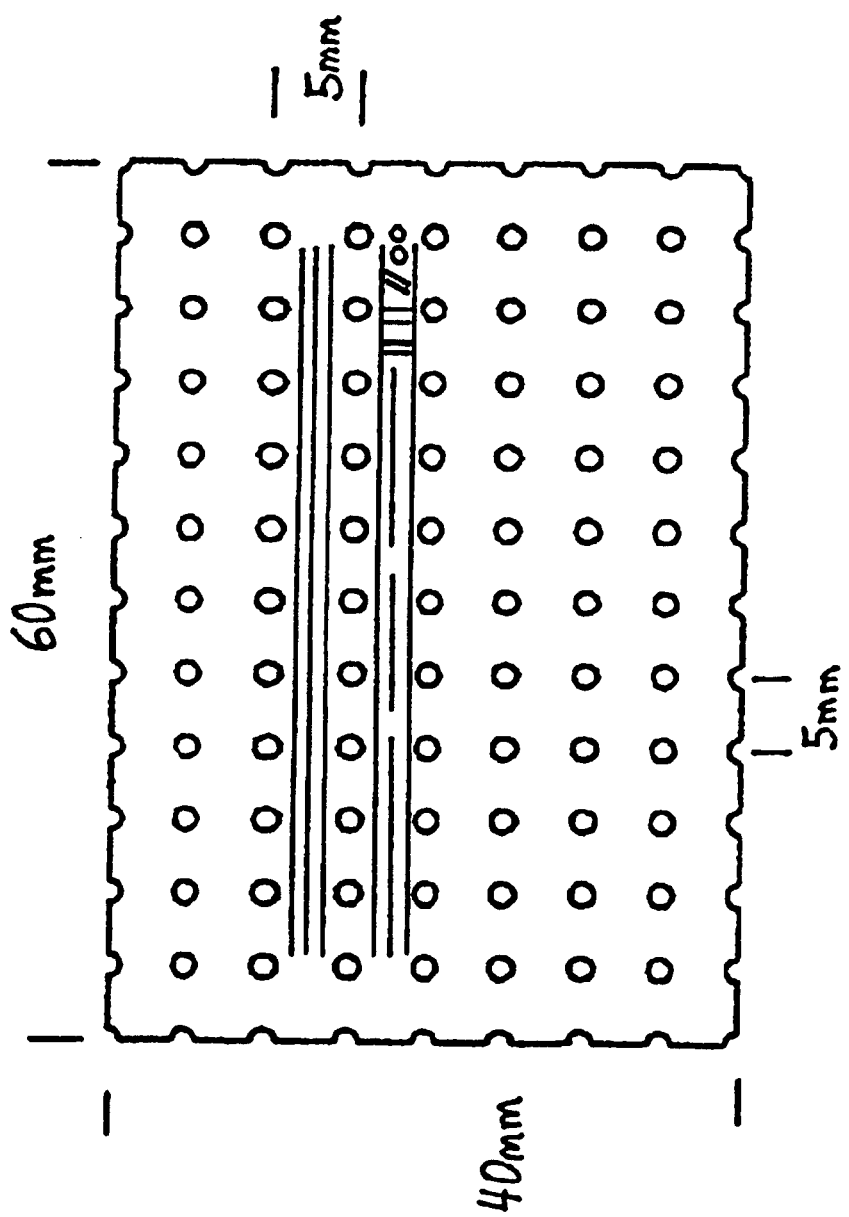

The upper corrugation shown in FIG. 12 comprises a relatively wide width, and an additional top corrugation, which extends above the base corrugation. The additional top corrugation is shown in the figure as a line between two other lines, which represent the base corrugation. The lines representing a corrugation beneath this corrugation is illustrated in the figure having a top corrugation, which is discontinuous. The top corrugation may comprise tiny transverse corrugations, having constant or different widths, or may comprise oval or circular protrusions. Any or all of the top corrugations or protrusions may, alternatively, comprise indents. Any combination of protrusions and/or indents is contemplated by the present invention. Additional stacking of protrusions and/or indents (such as indents having multiple layers (levels) in the base material of the resorbable sheet) are contemplated by the present invention.

Figure 13:
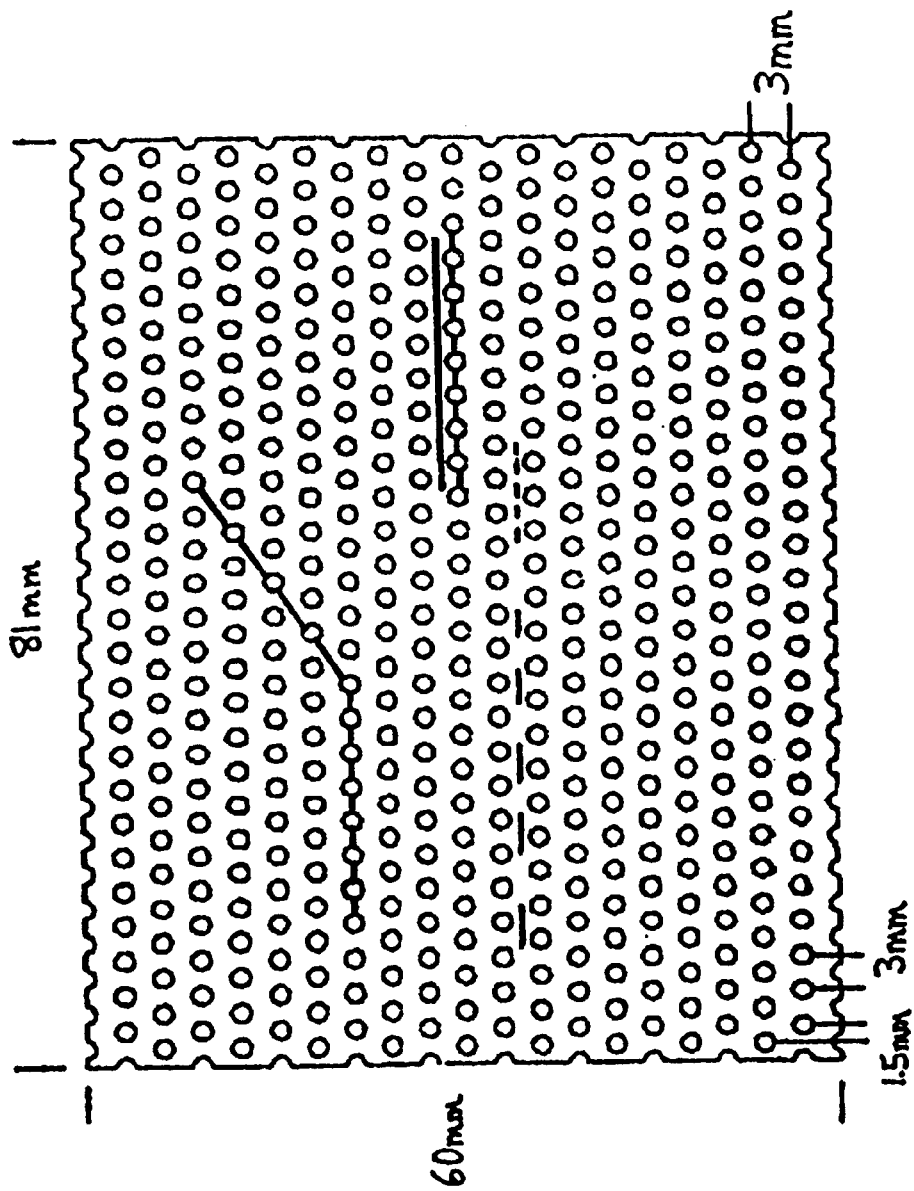

FIG. 13 illustrates additional embodiments of the present invention. The corrugations illustrated at the lower left portion of the resorbable sheet are disposed in a discontinuous fashion on the resorbable sheet. Similarly, the corrugation shown in the upper left and middle portion of the figure is discontinuous. The horizontal portion of the last-mentioned corrugation has an axes which generally intersects center portions of the apertures, and the diagonally extending portion of the corrugation has an axis which is generally off-axes with the center portions of the intersected apertures. The corrugation in the right hand portion of the figure is relatively wide, and is disposed off-axes with the adjacent apertures. Other combinations and variations of tissue guiding agents, membrane strengthening agents, protrusions, indents, and other configurations and modifications of the above-discussed elements are considered to be contemplated by the present invention.

In the below description, the embodiments may be constructed with or without tissue guiding agents and/or membrane strengthening agents. As an example of one inventive material that may be used in one embodiment, the resorbable sheet may comprise poly-caprolactone, which offers unique properties wherein bone has an enhanced propensity to bond to this material as compared to other resorbable materials.

Any of the above-mentioned tissue guiding agents and/or membrane strengthening agents may be constructed of a different material (which is adapted to provide any of a variety of possible properties, such as, for example, a medication, a strengthening agents, a tissue guiding agents, and/or a material having an enhanced propensity for bone to bond with the material) other than the base material of the resorbable sheet.

Alternatively, the base material may comprise a different material (which is adapted to provide any of a variety of possible properties, such as, for example, a medication, a strengthening agents, a tissue guiding agents, and/or a material having an enhanced propensity for bone to bond with the material) and the tissue guiding agents and/or membrane strengthening agents may comprise another, different material. Of course, the entire membrane, including the tissue guiding agents and/or membrane strengthening agents, may comprise a material having special properties, such as noted above in this paragraph. When the tissue guiding agents (and/or membrane strengthening agents) comprise a material having any of said special properties, and the material having special properties is different than the base material, then the tissue guiding agents, for example, do not need to comprise protrusions or recessed areas on the surface—the tissue guiding agents may be flush with the surface of the resorbable sheet but have a different composition than the base material. The protrusions and/or recessed areas, however, provide an increased surface interaction area to the resorbable sheet, which can be advantageous.

As a specific line of embodiments, any of the above-mentioned tissue guiding agents and/or membrane strengthening agents may be constructed of poly-caprolactone and the base not. Alternatively, the base material may comprise poly-caprolactone and the tissue guiding agents and/or membrane strengthening agents may comprise another material. Of course, the entire membrane, including the tissue guiding agents and/or membrane strengthening agents, may comprise poly-caprolactone.

Regarding, for example, the Summary of the Invention, lines 15–23 of page 11, one or more of the implants may be seeded onto the surface of the substantially planar sheet of non-metallic base material, as an alternative to, or in addition to the impregnation of the entire sheet of non-metallic base material. Substances, which can be impregnated into or onto the resorbable sheet, can comprise antibiotics, growth factors (for example, proteins), chemotherapeutic agents (e.g. anti-proliferation substances to treat cancer), anti-inflammatory drugs, pain medication, etc.

The resorbable sheet barrier limits new bone formation only to the area enclosed by the sheet. This allows for a three-dimensional regeneration of new tissue according to the volume enveloped by the membrane (controlled bone regeneration).

The material 44 is preferably thermally pliable. Since the material is preferably more pliable when heated to the glass transition temperature, a membrane of the material may be formed onto and/or around a bone. At any temperature below the glass transition temperature of 55–60 degrees, the sheet retains a relatively constant inherent strength. As the membrane cools to body temperature, the membrane loses pliability and regains its strength.

Below are specific inventive aspects and inventive applications of the resorbable membrane of the present invention. For dental applications, the resorbable membrane (sheet) thickness preferably ranges from about 100 to about 500 microns and, more preferably, is about 150 microns. Resorbable membranes of the present invention configured much. thinner than about 100 microns for dental applications are often times, but not always, too weak. The pore sizes preferably range from about 50 microns to about 1000 microns and, more preferably, range from about 50 microns to about 300 microns. The thin resorbable membranes of the present invention are less palpable in these dental applications, which allow for thin membranes due in part to the presence of soft-tissue pressure being relatively small. The soft tissue in dental applications is generally thinner and finer. Moreover, bone-graft or bone-graft substitutes are contemplated as being used often in these dental applications, in which case the resorbable membrane does not need to be as thick and strong. The apertures will help any infection occurring in the bone defect area to drain. Additionally, the bone defect areas in dental applications are typically small so the resorbable membrane can be configured to be relatively thin with a relatively high number of apertures. Also, in dental applications the resorbable membrane often does not have to be present for long, compared to other bone healing applications, so that the resorbable membrane can be manufactured to be relatively thin.

For intermediate-sized bone-defect areas, such as the-orbital floor, the aperture sizes preferably range from about 500 microns to about 2000 microns and, more preferably, are about 1500 microns in diameter. A preferred thickness of the resorbable membrane for this application is about 500 microns. The sizes of the apertures can be a function of the graft material, when grafts are used, so that, for example, smaller pores are used when a fine graft material is selected. The pore size to be used is generally a function of the type and condition of the local soft tissues. For example, if the periosteum is in tact then larger pores may be used, since in this case the resorbable membrane does not have to act as a guide to a regenerating periosteum. On the other hand, when the periosteum is damaged or absent then the resorbable membrane can act as a splint to some degree. The pore size may be a function of a concept of limited contact and graft containment so that when a smaller pore size is used the effective pore area of the resorbable membrane may be increased by adding more pores, for example.

The resorbable membrane of the present invention is also applicable to larger-sized bone defects, such as long bone; skull; flat bone, for example, around the crest to protect a bone graft harvest site; and spinal, where muscles in contact with the bone graft may cause the bone graft to resorb more quickly. The thickness of the membrane and pore size can be selected to control the resorption rate, wherein, for example, thicker membranes result in slower resorption. Generally, the longer the bone graft remains the greater is the amount of remodeling into the bone. For example, since cranial bone heals relatively slowly, the resorbable membrane can be formed having a relatively large thickness so that the resorbable membrane does not resorb too quickly. For these large and even larger applications, resorbable membranes having thicknesses preferably ranging from about 1000 microns to about 2000 microns and preferably having aperture sizes ranging from about 500 microns to about 2000 microns can be selected. A preferred configuration comprises a thickness of 1000 microns and apertures sizes of about 1500 microns.

Regarding bridge dimensions, wherein the bridge is defined as the portion of the resorbable membrane between pores, an object of the present invention is in some instances to maximize the porosity, while maintaining adequate strength. Accordingly, bridge dimensions can be optimized in accordance with the desired porosity and the desired rigidity for a particular application. A large number of the above-described principles of the present invention are applicable to other mammals as well.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. An implant for protecting a tissue defect, the implant having a pre-implant configuration defined as a configuration of the implant immediately before being implanted over the tissue defect, the implant having a first side and a second side, and comprising:
    a layer of polymer base material between the first side and the second side;
    a plurality of apertures disposed in the layer of polymer base material, at least a majority of the plurality of apertures of the implant when the implant is in the pre-implant configuration having diameters ranging from about 20 microns to about 3500 microns and defining isolated fluid-flow paths extending from the first side to the second side; and
    at least one formation other than the plurality of apertures disposed in the layer of polymer base material.

2. The implant as set forth in claim 1, wherein the tissue defect comprises a bone defect.

3. The implant as set forth in claim 1, wherein the at least one formation comprises a tissue guiding agent, the tissue guiding agent being constructed to guide a growth of tissue in at least one predetermined direction.

4. The implant as set forth in claim 3, wherein the layer of polymer base material is at least partially resorbable so that within about 24 months after implantation it loses at least a portion of its mechanical strength.

5. The implant as set forth in claim 3, wherein the tissue guiding agent comprises a corrugation.

6. The implant as set forth in claim 3, wherein the tissue guiding agent comprises at least one corrugation, the at least one corrugation having a length and a width, the width varying substantially along a portion of the length of the at least one corrugation.

7. The implant as set forth in claim 3, wherein the tissue guiding agent comprises a first corrugation having a length and a width, and further comprises a second corrugation having a length and a width, the width of the first corrugation being substantially greater than the width of the second corrugation.

8. The implant as set forth in claim 3, wherein the tissue guiding agent comprises a first corrugation having a length, a width and a height, and further comprises a second corrugation having a length, a width, and a height, the height of the first corrugation being substantially greater than the height of the second corrugation.

9. The implant as set forth in claim 3, wherein the tissue guiding agent comprises at least one corrugation, the at least one corrugation having a length, a width and a height, the height varying substantially along a portion of the length of the at least one corrugation.

10. The implant as set forth in claim 5, wherein the corrugation comprises a protrusion.

11. The implant as set forth in claim 3, wherein the corrugation comprises an indent.

12. The implant as set forth in claim 3, wherein the tissue guiding agent comprises a plurality of corrugations extending from one side of the implant to another side of the implant.

13. The implant as set forth in claim 12, wherein the one side comprises the first side and the other side comprises the second side.

14. The implant as set forth in claim 13, wherein at least one of the plurality of corrugations extends through at least one of the plurality of apertures.

15. The implant as set forth in claim 11, wherein:
    the tissue guiding agent comprises a plurality of corrugations;
    at least two corrugations of the plurality of corrugations have axes which are perpendicular to one another.

16. The implant as set forth in claim 3, wherein the tissue guiding agent comprises a plurality of corrugations having axes which pass through a common area on the implant.

17. The implant as set forth in claim 16, wherein at least two corrugations of the plurality of corrugations are not perpendicular to one another.

18. The implant as set forth in claim 16, wherein each of the plurality of corrugations extends substantially radially from the common area.

19. The implant as set forth in claim 18, wherein the common area comprises one of the plurality of apertures.

20. The implant as set forth in claim 18, wherein a surface area occupied by the common area ranges from about 20 microns to about 3500 microns.

21. The implant as set forth in claim 16, wherein:
    the common area comprises a common point; and
    all of the plurality of corrugations intersect at the common point.

22. The implant as set forth in claim 3, wherein the tissue guiding agent comprises a plurality of parallel corrugations.

23. The implant as set forth in claim 22, wherein a given corrugation of the plurality of parallel corrugations is aligned in a direction of growth of the tissue to be regenerated.

24. The implant as set forth in claim 22, wherein the tissue guiding agent comprises at least one corrugation having an axis that is not parallel to an axis of the given corrugation.

25. The implant as set forth in claim 3, wherein the tissue guiding agent is disposed on only one of the first side and the second side.

26. The implant as set forth in claim 3, wherein the tissue guiding agent is disposed on both the first side and the second side.

27. The implant as set forth in claim 3, wherein the tissue guiding agent comprises a material having an enhanced propensity for bone to bond with it, relative to a propensity of the layer of base material for bone to bond with it.

28. The implant as set forth in claim 27, wherein the tissue guiding agent comprises poly-caprilactone.

29. The implant as set forth in claim 3, wherein the tissue guiding agent comprises a medication.

30. The implant as set forth in claim 3, wherein the tissue guiding agent is formed within the layer of polymer base material and does not disrupt a surface of the implant.

31. The implant as set forth in claim 3, wherein the tissue guiding agent comprises a resorbable substance, which loses a portion of its mechanical strength within about 24 months after implantation.

32. The implant as set forth in claim 3, wherein the tissue guiding agent comprises a non-resorbable substance, which does not lose a portion of its mechanical strength within about 24 months after implantation.

33. The implant as set forth in claim 3, wherein the tissue guiding agent comprises a resorbable substance, which loses a portion of its mechanical strength within about 24 months after implantation.

34. The implant as set forth in claim 3, wherein the at least one formation comprises a strengthening agent.

35. The implant as set forth in claim 34, wherein the strengthening agent is formed within the layer of polymer base material and does not disrupt a surface of the implant.

36. The implant as set forth in claim 34, wherein the layer of polymer base material is resorbable, so that it loses at least a portion of its mechanical strength within about 24 months after implantation.

37. The implant as set forth in claim 36, wherein the strengthening agent comprises a non-resorbable substance, which does not lose a portion of its mechanical strength within about 24 months after implantation.

38. The implant as set forth in claim 34, wherein the strengthening agent comprises a resorbable substance, which loses a portion of its mechanical strength within about 24 months after implantation.

39. The implant as set forth in claim 34, wherein the strengthening agent comprises at least one fiber.

* * * * *